United States Patent
Seo et al.

(10) Patent No.: US 6,646,139 B2
(45) Date of Patent: Nov. 11, 2003

(54) PROCESS FOR PRODUCING PROPYLENE OXIDE

(75) Inventors: Tateo Seo, Chiba (JP); Junpei Tsuji, Ichihara (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 10/220,501

(22) PCT Filed: Mar. 19, 2001

(86) PCT No.: PCT/JP01/02190

§ 371 (c)(1),
(2), (4) Date: Oct. 30, 2002

(87) PCT Pub. No.: WO01/70714

PCT Pub. Date: Sep. 27, 2001

(65) Prior Publication Data

US 2003/0139615 A1 Jul. 24, 2003

(30) Foreign Application Priority Data

Mar. 24, 2000 (JP) .......................................... 2000-083957

(51) Int. Cl.[7] ............................................. C07D 301/19
(52) U.S. Cl. ....................................... 549/529; 549/523
(58) Field of Search .................................. 549/529, 523

(56) References Cited

U.S. PATENT DOCUMENTS

| | | |
|---|---|---|
| 3,350,422 A | 10/1967 | Kollar |
| 5,723,637 A | 3/1998 | Tsuji et al. |

FOREIGN PATENT DOCUMENTS

JP       50-70310 A       6/1975

*Primary Examiner*—Ba K. Trinh
(74) *Attorney, Agent, or Firm*—Sughrue Mion, PLLC

(57) ABSTRACT

A process for producing propylene oxide, which comprises steps described below, wherein the concentration of ethylbenzene in a solution containing isopropylbenzene to be recycled to the oxidation step is 10% by weight or less:

oxidation step; a step in which isopropylbenzene is oxidized to obtain isopropylbenzene hydroperoxide, epoxidation step; a step in which isopropyl hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

3 Claims, No Drawings

PROCESS FOR PRODUCING PROPYLENE OXIDE

This application is a 371 of PCT/JP01/02190 filed on Mar. 19, 2001.

TECHNICAL FIELD

The present invention relates to a process for producing propylene oxide. More particularly, the invention relates to a process for producing propylene oxide, wherein said process for producing propylene oxide has excellent characteristics that propylene is converted to propylene oxide using isopropylbenzene hydroperoxide obtained from isopropylbenzene, as an oxygen carrier, that said isopropylbenzene can be repeatedly used, that the reaction volume in each step can be effectively utilized, and that epoxidation reaction can be effectively carried out thereby being able to produce propylene oxide effectively.

BACKGROUND ART

A process in which propylene is oxidized using ethylbenzene hydroperoxide as an oxygen carrier to give propylene oxide and styrene is known as Halcon process. Since, in this process, styrene is inevitably produced together with propylene oxide, it is unsatisfactory from the viewpoint that only propylene oxide is to be selectively produced.

On the other hand, a concept of a process in which propylene is converted to propylene oxide using isopropylbenzene hydroperoxide obtained from isopropylbenzene, as an oxygen carrier, and said isopropylbenzene is repeatedly used, is described in Czechoslovak Patent No. CS 140,743. The process described in said patent does not contain precise descriptions concerning necessary steps except an oxidation step, epoxidation step and hydrogenolysis step. Various problems arise in practical recycling of isopropylbenzene and therefore the descriptions cannot be said as sufficient for industrial realization.

DISCLOSURE OF THE INVENTION

Under such circumstances, an object of the present invention is to provide a process for producing propylene oxide, having excellent characteristics that propylene is converted to propylene oxide using isopropylbenzene hydroperoxide obtained from isopropylbenzene, as an oxygen carrier, that said isopropylbenzene can be repeatedly used, that there action volume in each step can be effectively utilized, and that epoxidation reaction can be effectively carried out thereby being able to produce propylene oxide effectively.

Namely, the invention relates to a process for producing propylene oxide, which comprises steps described below, wherein the concentration of ethylbenzene in a solution containing isopropylbenzene to be recycled to the oxidation step is 10% by weight or less:

oxidation step; a step in which isopropylbenzene is oxidized to obtain isopropylbenzene hydroperoxide, epoxidation step; a step in which isopropyl hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

BEST MODE FOR CARRYING OUT THE INVENTION

The oxidation step in the present invention is a step in which isopropylbenzene is oxidized to obtain isopropylbenzene hydroperoxide. The oxidation of isopropylbenzene is usually effected by autoxidation with oxygen-containing gas such as the air, an oxygen-enriched air or the like. The oxidation reaction may be carried out without any additive or with an additive such as an alkali. The reaction temperature is usually 50 to 200° C., and the reaction pressure is usually between the atmospheric pressure and 5 MPa. In the oxidation with an additive, the alkali includes alkali metal compounds such as NaOH, KOH; alkaline earth metal compounds; alkali metal carbonates such as $Na_2CO_3$, $NaHCO_3$; ammonia; $(NH_4)_2CO_3$; alkali metal ammonium carbonates and the like.

The epoxidation step in the present invention is a step in which isopropylbenzene hydroperoxide obtained in the oxidation step is reacted with propylene to obtain propylene oxide and cumyl alcohol. From a viewpoint that the desired product should be obtained in a high yield and under a high selectivity, the epoxidation step is preferably conducted in the presence of a catalyst containing a titanium-containing silicon oxide. The catalyst is preferably a catalyst containing titanium chemically bound to silicon oxide, so-called titanium-silica catalyst. Examples may include products in which a titanium compound is supported on a silica carrier, products in which a titanium compound is compounded with a silicon oxide by a co-precipitation or sol-gel method, titanium-containing zeolite compounds or the like.

In the present invention, isopropylbenzene hydroperoxide used as the raw material for the epoxidation step may be a dilute or thick purification or non-purification product.

The epoxidation reaction is carried out by contacting propylene and isopropylbenzene hydroperoxide with a catalyst. The reaction can be conducted in a liquid phase using a solvent. The solvent must be a liquid under the reaction temperature and pressure, and substantially inert to the reactants and the product. The solvent may be composed of a substance existing in a solution of the hydroperoxide used. When, for example, isopropylbenzene hydroperoxide is a mixture with isopropylbenzene as the raw material, it is also possible to use said material, without adding a solvent in particular, as the solvent. Other useful solvents include aromatic single-ring compounds (for example, benzene, toluene, chlorobenzene and o-dichlorobenzene), alkane (for example, octane, decane and dodecane) and the like. The epoxidation temperature is generally 0 to 200° C. and preferably 25 to 200° C. The pressure may be any pressure sufficient to keep liquid state of the reaction mixture. Generally, the pressure is advantageously 100 to 10,000 kPa.

The epoxidation can advantageously be carried out with a catalyst in the form of a slurry or a fixed-bed. The fixed-bed is preferred in the case of a large-scale industrial operation. In addition, the reaction can be carried out by a batch process, a semi-continuous process, a continuous process or the like. When a liquid containing the raw materials for reaction is passed through a fixed-bed, the catalyst is not contained at all or substantially in a liquid mixture discharged from a reaction zone.

The hydrogenolysis step in the present invention is a step in which cumyl alcohol obtained in the epoxidation step is subjected to hydrogenolysis to obtain isopropylbenzene, and said isopropylbenzene is recycled to the oxidation step as the raw material for the oxidation step. In other words, the same product, i.e. isopropylbenzene, used in the oxidation step is recovered. The hydrogenolysis is usually carried out by contacting cumyl alcohol and hydrogen with a catalyst. The reaction can be conducted in a liquid phase using a solvent or in a gaseous phase. The solvent must be substantially inert to the reactants and the product. The solvent may comprise a substance existing in a solution of the cumyl alcohol used. When, for example, cumyl alcohol is a mixture with isopropylbenzene as the product, it is possible to use this, without adding a solvent in particular, as the solvent. Other useful solvents include alkane (for example, octane, decane and dodecane), aromatic single-ring compounds (for example, benzene, ethylbenzene and toluene), and others. The temperature for the hydrogenolysis reaction is generally 0 to 500° C. and preferably 30 to 400° C. Generally, the pressure is advantageously 100 to 10,000 kPa. The hydrogenolysis can advantageously be carried out with a catalyst in the form of a slurry or a fixed-bed. Any catalyst having a hydrogenation ability can be used as the catalyst. Examples of the catalyst include metal catalysts of metals of the group 8th to 10th such as cobalt, nickel, palladium and the like, and metal catalysts of metals of the group 11th or 12th such as copper, zinc and the like, and copper catalysts are preferred from the viewpoint that by-products are suppressed. The copper catalysts include copper, Raney copper, copper-chromium, copper-zinc, copper-chromium-zinc, copper-silica, copper-alumina and the like. The process of the present invention can be carried out by a batch process, a semi-continuous process or a continuous process. When a solution or gas containing the raw materials for reaction is passed through a fixed-bed, the catalyst is not contained at all or substantially in a liquid mixture discharged from the reaction zone.

In the present invention, it is necessary that the concentration of ethylbenzene in a solution containing isopropylbenzene to be recycled to the oxidation step is controlled to 10% by weight or less, preferably 5% by weight or less. Ethylbenzene is produced in the hydrogenolysis step as the result of hydrogenation of acetophenone which is formed by decomposition of isopropylbenzene hydroperoxide in the oxidation step and epoxidation step. Ethylbenzene is a component accumulated in the system, and its concentration increases with time by continuous recycling. This cause a decrease in effective reaction volume in each of the steps, and inhibition of the reaction in the epoxidation step due to by-products derived from ethylbenzene as well as an inconvenience that said by-products might be impurities in propylene oxide. In consideration of effective utilization of the reaction volume and suppression of by-products, it is necessary to control the concentration of ethylbenzene in the solution containing isopropylbenzene to be recycled to the oxidation step within a range specified in the present invention. Methods for controlling the concentration of ethylbenzene may be anyone of methods in which all or part of ethylbenzene is removed to outside of the system of steps in the preset invention by distillation, extraction or the like, methods in which the compound is converted to another compound, methods in which the concentration of the compound is lowered by an adsorbent or the like, and so on. In the case of removal to outside of the system, the step for removing ethylbenzene (hereinafter, may be referred to as "ethylbenzene-removing step") can be carried out in at least one place of the oxidation step, epoxidation step and hydrogenolysis step or in at least one place between which the steps are connected, usually by distillation, extraction or the like, and it is preferred to carry out distillation after the hydrogenolysis step in which a difference between boiling points of the useful component and ethylbenzene become the largest, from viewpoints of decreasing loss of the useful component and of minimizing energy for distillation. Moreover, in the present invention, the concentration of organic acids in the solution containing isopropylbenzene hydroperoxide to be supplied to the epoxidation step is preferably 0.5% by weight or less and more preferably 0.1% or less. By specifying within this range, the activity of the catalyst used in the epoxidation step can be maintained at a high level and the life of the catalyst can be kept for longer time.

Additionally, in the present invention, the concentration of phenol in the solution containing isopropylbenzene to be recycled to the oxidation step is preferably 5% by weight or less. These allow effective utilization of the volume for the reaction in each step and effective accomplishment of oxidation reaction and epoxidation reaction.

Moreover, in the present invention, the hydrogen ion concentration (pH) in the solution containing isopropylbenzene to be recycled to the oxidation step is preferably 5 to 10. This allows maintenance of the yield in the oxidation step at a high level. Herein, pH refers to a value obtained by the following measurement: That is, the solution of isopropylbenzene is mixed with water at a weight ratio of 1:1; after shaking the mixture sufficiently, pH of an aqueous phase separated out of an oil layer is measured to give the value.

Furthermore, in the present invention, the concentration of cumene dimer in the solution containing isopropylbenzene to be recycled to the oxidation step is preferably 5% by weight or less. This allows effective utilization of the volume for the reaction in each step and prevention of stoppage trouble in the system.

EXAMPLE 1

Oxidation Step

Isopropylbenzene recycled from the hydrogenolysis step (wherein the concentration of ethylbenzene in a solution containing isopropylbenzene to be recycled to the oxidation step is less than 10% by weight) is mixed with the air and reacted under conditions including a pressure of 300 kPa and a temperature of 150° C. for 5 hours. The produced oxidized solution has the following composition:

Composition of Oxidation Solution:

| | |
|---|---|
| isopropylbenzene hydroperoxide | 35% by weight |
| cumyl alcohol | 2% by weight |
| isopropylbenzene | 60% by weight |
| acetophenone | 0.1% by weight |
| ethylbenzene | 0.5% by weight |

Epoxidation Step

The oxidized solution which is obtained in the oxidation step, is continuously passed through a fixed-bed flowing reactor in the presence of titanium-containing silicon oxide catalyst together with 10 times by mol of propylene per mol of isopropylbenzene hydroperoxide contained in the oxidized solution. By controlling the temperature at the inlet, the conversion of isopropylbenzene hydroperoxide is maintained at 99% and stabilized at stationary state. At this state, the reaction temperature is 60° C. and the selectivity is 95%. Lower boiling components such as propylene, propylene oxide and the like are separated and recovered. The obtained reaction solution has the following composition:

Composition of Epoxidized Solution:

| | |
|---|---|
| isopropylbenzene hydroperoxide | 0.4% by weight |
| cumyl alcohol | 33.5% by weight |
| isopropylbenzene | 62.3% by weight |

| acetophenone | 0.6% by weight |
| ethylbenzene | 0.5% by weight |

Hydrogenolysis Step

The reaction solution which is obtained in the epoxidation step is continuously passed through a fixed-bed flowing reactor in the presence of copper-chromium catalyst together with 2 times by mol of hydrogen per mol of cumyl alcohol in the reaction liquid. By controlling the temperature at the inlet, almost 100% of cumyl alcohol is converted. At this state, the reaction temperature is 180° C. The obtained hydrogenolysis solution has the following composition:
Composition of Hydrogenolysis Solution:

| isopropylbenzene hydroperoxide | 0% by weight |
| cumyl alcohol | 0% by weight |
| isopropylbenzene | 96.1% by weight |
| acetophenone | 0.0% by weight |
| ethylbenzene | 1.1% by weight |

Ethylbenzene-Removing Step

Ethylbenzene is removed from the hydrogenolysis solution obtained in the hydrogenolysis step by distillation. An oil layer which is obtained has the following composition:
Composition of Ethylbenzene-Removed Solution:

| isopropylbenzene hydroperoxide | 0% by weight |
| cumyl alcohol | 0% by weight |
| isopropylbenzene | 96.6% by weight |
| acetophenone | 0.0% by weight |
| ethylbenzene | 0.5% by weight |

COMPARATIVE EXAMPLE 1

When oxidation, epoxidation and hydrogenolysis are carried out under similar conditions to those in Example 1 except that removal of ethylbenzene is not carried out. The concentration of ethylbenzene in the oil layer to be recycled continuously increases. As the result, the concentration of ethylbenzene in the solution containing isopropylbenzene to be recycled to oxidation step exceeds 10% by weight and effective utilization of the reaction volume in each step becomes impossible. In addition, the catalyst in the epoxidation step is poisoned and its activity gradually drops.

INDUSTRIAL APPLICABILITY

As described above, according to the present invention, there can be provided a process for producing propylene oxide, having excellent characteristics that propylene is converted to propylene oxide using isopropylbenzene hydroperoxide obtained from isopropylbenzene, as an oxygen carrier, that said isopropylbenzene can repeatedly be used, that the reaction volume in each step can be effectively utilized, and that epoxidation reaction can be effectively carried out thereby being able to produce propylene oxide effectively.

What is claimed is:

1. A process for producing propylene oxide, which comprises steps described below, wherein the concentration of ethylbenzene in a solution containing isopropylbenzene to be recycled to the oxidation step is 10% by weight or less:

oxidation step; a step in which isopropylbenzene is oxidized to obtain isopropylbenzene hydroperoxide, epoxidation step; a step in which isopropyl hydroperoxide obtained in the oxidation step is reacted with propylene to obtain propylene oxide and cumyl alcohol, and hydrogenolysis step; a step in which cumyl alcohol obtained in the epoxidation step is subjected to hydrogenolysis to obtain isopropylbenzene, and said isopropylbenzene is recycled to the oxidation step as a raw material for the oxidation step.

2. The process according to claim 1, comprising a step for removing ethylbenzene to outside of the system in at least one place of the steps or between which the steps are connected.

3. The process according to claim 1 or 2, wherein the concentration of ethylbenzene is 5% by weight or less.

* * * * *